US010939942B2

(12) United States Patent
Forsell

(10) Patent No.: US 10,939,942 B2
(45) Date of Patent: Mar. 9, 2021

(54) COMPOSITION, METHOD AND DEVICE FOR STABILIZING IMPLANTED HYDRAULIC DEVICES

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 0 days.

(21) Appl. No.: 15/620,494

(22) Filed: Jun. 12, 2017

(65) Prior Publication Data

US 2017/0273726 A1 Sep. 28, 2017

Related U.S. Application Data

(63) Continuation of application No. 13/123,574, filed as application No. PCT/SE2009/051133 on Oct. 9, 2009, now Pat. No. 9,675,390.

(Continued)

(30) Foreign Application Priority Data

Oct. 10, 2008 (SE) ...................................... 0802156

(51) Int. Cl.
*A61B 17/70* (2006.01)
*A61B 17/88* (2006.01)
(Continued)

(52) U.S. Cl.
CPC ...... *A61B 17/7097* (2013.01); *A61B 17/7094* (2013.01); *A61B 17/7095* (2013.01);
(Continued)

(58) Field of Classification Search
CPC ............ A61B 17/7094; A61B 17/7095; A61B 17/7097; A61B 17/8802; A61B 17/8841; A61L 27/502; A61L 27/505
See application file for complete search history.

(56) References Cited

U.S. PATENT DOCUMENTS 5,843,156 A * 12/1998 Slepian .................. A61F 2/062
128/898
5,964,261 A * 10/1999 Neuenfeldt ........... A61F 2/0095
141/100
(Continued)

FOREIGN PATENT DOCUMENTS

WO WO 2007133214 A1 * 11/2007 ............. A61F 2/441

*Primary Examiner* — William H Matthews

(57) ABSTRACT

A method for stabilizing a leaking implanted device capable of being hydraulically adjusted by introducing or withdrawing hydraulic fluid to/from the device, the device having an inner space for enclosing the hydraulic fluid. The method comprises at least one of the steps of introducing at least one of: a solidifying fluid, an initiator adapted to exert influence on a solidifying fluid or the hydraulic fluid, and a mixture of a solidifying fluid and an initiator, into said leaking implanted hydraulically adjustable device for solidifying the solidifying fluid or the hydraulic fluid for permanently defining the volume and/or shape of the device, and repairing a leakage, puncture or rupture of the implanted hydraulically adjustable device by the introduction of a sealing component which forms a layer on the inside of the implanted hydraulically adjustable device preventing further leakage with retained function of the device, such that the repaired implanted hydraulically adjustable device can be hydraulically adjusted by introducing or withdrawing fluid to/from the device.

11 Claims, 3 Drawing Sheets

Related U.S. Application Data

(60) Provisional application No. 61/213,165, filed on May 13, 2009.

(51) Int. Cl.
    *A61F 5/00* (2006.01)
    *B29C 73/02* (2006.01)

(52) U.S. Cl.
    CPC ...... *A61B 17/8802* (2013.01); *A61B 17/8841* (2013.01); *A61F 5/0056* (2013.01); *A61F 5/0059* (2013.01); *B29C 73/02* (2013.01); *B29C 73/025* (2013.01)

(56) References Cited

U.S. PATENT DOCUMENTS

| | | | |
|---|---|---|---|
| 2005/0015140 A1* | 1/2005 | deBeer | A61B 17/68 623/1.21 |
| 2006/0127246 A1* | 6/2006 | Forsell | A61M 5/1428 417/412 |

* cited by examiner

COMPOSITION, METHOD AND DEVICE FOR STABILIZING IMPLANTED HYDRAULIC DEVICES

This application is a continuation of U.S. application Ser. No. 13/123,574, filed on 2011 Apr. 11, which is the U.S. national phase of International Application No. PCT/SE2009/051133, filed on 2009 Oct. 9, which claims the benefit of U.S. Provisional Application 61/213,165, filed on 2009 May 13, and Swedish Patent Application 0802156-0, filed Oct. 10, 2008, the entire contents of each of which are hereby incorporated by reference.

TECHNICAL FIELD

The present invention relates to the field of implanted medical devices, their operation and maintenance. The invention concerns in particular implanted hydraulic devices and the stabilization of hydraulic elements in such devices.

BACKGROUND

The field of biomechanics, including implanted medical devices, is constantly growing. Today, implants are no longer limited to static parts, simply replacing damaged, diseased or surgically removed tissue, organs, or limbs of the body. Instead, a growing number of implants combine advanced electronic, mechanic and in many cases, hydraulic mechanisms, mimicking or replacing functions of the body, supporting or even augmenting functions of the body.

The hydraulic mechanism can be one of compression or restriction, achieved by a hydraulic member acting on at least one body part, organ or tissue. The hydraulic mechanism can also be one of actuation, where a hydraulic member causes a body part to move. The hydraulic mechanism can also be one of filling, extending, applying torque, expanding or otherwise adjusting body parts, organs or tissue, where the hydraulic member acts on the size, shape or position of a body part, organ or tissue.

One example is the adjustable gastric band (disclosed for example in WO 00/00108) used e.g. in the treatment of obesitas. In this example, a band is surgically placed around the stomach, reducing the opening in the cardia region, or around the stomach, creating a small gastric pouch, both methods effectively limiting the food intake of the obese subject. An adjustable gastric band has a considerable advantage: the tightness of the gastric band can be adjusted without the need for repeated operations. Hydraulic gastric bands are one sub-group of adjustable gastric bands. The tightness of the band is adjusted by injecting or withdrawing a fluid present inside the band. This can be controlled within the body, through the provision of a reservoir of said fluid, coupled to a pump or similar device. Alternatively, the fluid can be injected or withdrawn externally, for example through an access port or injection port. When fluid is introduced, the band places pressure around the outside of the stomach, restricting the movement of food. Frequently the tightness of the band is adjusted during several visits to the doctor, until optimal restriction has been achieved. There are currently several gastric bands on the market, so far however regulated through an injection port.

Other types of hydraulic implants include artificial sphincters for controlling the flow in various ducts in the body, e.g. the anal, urethral, pancreal or bile ducts; artificial valves controlling the blood flow to different body parts; hydraulic corpus cavernosum implants for treating erectal dysfunction; hydraulic implanted braces for vertebral adjustments, such as the treatment of scoliosis; adjustable breast implants etc, all products which are currently in different phases of development, testing or use. A non-exclusive list of examples includes the male sexual impotence treatment apparatus described in EP 1 563 814 B1, the anal incontinence treatment apparatus described in EP 1 584 303 B1, and the hydraulic urinary incontinence treatment apparatus described in EP 1 263 355 B1.

In all hydraulic applications, implanted or not, there is a small risk of rupture of membranes, tubing, couplings, connectors, pumps and valves etc, and consequently a leakage of the hydraulic fluid used may take place. Also other implants, functioning through mechanical or electrical mechanism may loose their integrity and suffer from ruptures, leaks and the like. In an implanted device, a leakage may be particularly problematic, both as it is more difficult to detect, and as a leakage can have negative consequences for the patient's health. In many cases, saline is used in order to minimize the consequences of possible leaks. Even when the leakage itself does not constitute a health issue, the function of the implant will be impaired. A leaking hydraulic implant will inevitably loose its internal pressure, which in turn influences its function. The implant will no longer retain its desired volume, shape or position. For example a hydraulic implanted brace will no longer act on the vertebrae with the same force and will not be able to retain the desired position. Similarly, a hydraulic implanted artificial sphincter will no longer be able to prevent leakage of urine or faeces.

While immediate repair or replacing the implant would be the most desirable action, it is perhaps not always possible. It may be difficult to schedule an operation, or the patient may be too weak to undergo anaesthesia and surgical intervention. For these and other reasons, it would be desirable if a leaking implant could be repaired, permanently or temporarily, without the need of hospitalizing the patient.

In an entirely different technical field, namely the automotive industry, different solutions for repairing tires have been developed. According to one principle, the punctured tire is filled with a propellant and a foam-forming sealant material which expands and cures inside the tire, restoring the shape and pressure of the tire. According to another principle, a solution is introduced through the valve and forms a sealing layer, or lining, on the inside of the tire, where after the tire can be inflated again. In a combination of the two principles, the foam also acts as a sealant.

In the first case, the foam forming material is usually polyurethane. Other examples include polyisoprene and ethylene-propylene-diene terpolymer elastomer (EPDM).

In the second case, a polymer solution including for example polybutene, polypropylene or butyl rubber is used. Alternatively, a thixotropic polymer gel is used. Examples of such gels include, but are not limited to, acrylic polymers. The thixotropic properties of the gel make it possible to introduce it through the valve, and when the tire rotates, the gel will spread evenly over the inner surface. When the vehicle stops, the gel will become more rigid and substantially remain evenly spread inside the tire.

These repair kits and solutions are commercially available and frequently included in new cars, as a space and weight saving alternative to the traditional spare tire.

WO 2004/052248 discloses a method and apparatus for intervertebal disc expansion, wherein a biomaterial is injected into an intradiscal space where it undergoes transition from a flowable to a non-flowable state. The biomaterial can be injected directly into a space within the disc annulus, or into a balloon-like element introduced into the disc annulus.

WO 2007/133214 discloses devices for prosthetic disc replacement and soft-tissue reconstruction wherein an implanted device is inflated with a suitable gallant or combination of gellants. The disclosure of the '214 publication addresses the issue of leaking implants and teaches the use of gel forming fillers, where a flexible empty or partially filled pouch is implanted into a selected site in a human body, where after at least one type of gallant is injected into the pouch, wherein the gallant solidifies within the pouch and forms a solidified medical device of a desired shape.

US 2005/0015140 A1 relates to three-dimensional space filling implantable devices which may be filled with an bioactive agent. The '140 publication and describes an encapsulation device configured to receive a fluid to expand the device to conform to the shape. An important aspect of said device is a self-sealing valve, configured to open to receive one or more fluids and close to prevent leakage into the body.

WO 01/87195 concerns a method and apparatus for treating interverbal disks, describing the heating and injection of thermoplastic material, e.g. gutta percha, either directly into an existing cavity in the body, or into a cavity created by expanding an expandable member. The heated thermoplastic material is flowable at an elevated temperature, but solidifies at body temperature.

There remains a need for improved methods and compositions. Further, the background art does not address problems encountered with implants having more complex functions. Thus, one objective underlying various embodiments of the invention is to make it possible to repair and/or stabilize, temporarily or permanently, a leaking implanted device, such as an implanted hydraulic device.

Another objective is to stabilize an implanted device, for example in the sense that the position, shape or volume of the device or a hydraulic element forming part of the device, is permanently fixed.

Further objectives of the invention, as well as advantages associated with embodiments of the invention, will become evident to a skilled person upon a closer study of the present description, non-limiting examples, claims and drawings.

SUMMARY

The present invention makes available a method, composition and kit for the stabilization of implanted devices in the animal body, without the need for hospitalization or surgical intervention.

One embodiment comprises a method for stabilizing an implanted hydraulic device having an inner space enclosing a fluid, wherein said fluid is solidified through the influence of an initiator added to, or exerting influence on said fluid. Preferably said stabilizing involves the repair of a leakage, puncture or rupture of the implanted device or parts thereof and wherein the solidified fluid prevents further leakage of the fluid with retained function of the device. The stabilizing may preferably also involve the repair of a leakage or rupture of the implanted device and wherein the solidified fluid prevents further leakage of the fluid and permanently defines the volume and/or shape of the device.

When the fluid enclosed in the device comprises a curable component, the initiator added to said fluid is preferably chosen from a polymerization initiator, a cross-linking agent, and a catalyst. Alternatively, when the fluid enclosed in the device comprises a curable component, the solidification can be initiated by subjecting the fluid to radiation, or by subjecting said fluid to a change in temperature.

According to an embodiment, said initiator is included in a second fluid substantially replacing said first fluid.

Alternatively, said fluid is substantially replaced by a second fluid introduced in flowable form, which second fluid has a melting point sufficiently above normal body temperature so as to solidify at body temperature, but not as high as to compromise the health of the patient when in flowable or molten form.

According to an embodiment above, wherein the second fluid solidifies when exposed to an initiator, and wherein said hydraulic device implanted in the body does not contain said initiator, the method preferably includes the steps of:
introducing an initiator into said fluid,
mixing said initiator and said fluid, and
introducing the resulting mixture into said hydraulic device.

In the above embodiment said initiator is chosen from air, nitrogen, and oxygen. Alternatively, said initiator is chosen from a polymerization initiator, a cross-linking agent, and a catalyst Further, where the initiator is a component capable of solidifying when exposed to water or moisture, water or moisture is preferably added to said component either before or after introduction of said component into the implanted device.

The initiator is preferably a biocompatible component.

In any one of the above embodiments, the initiator and at least one chamber holding the same are kept under sterile conditions. The method preferably comprises the use of a sterile reservoir containing the initiator, and further includes a step of moving the sterile initiator from said reservoir into the implanted hydraulic device under sterile conditions.

In a method where the initiator comprises two sterile substances, the method preferably includes a step of mixing said substances under sterile conditions before the introduction of said substances into the body.

A method according to the invention preferably comprises the steps of:
keeping a first component of the initiator separated from a second component of the initiator, both components being biocompatible materials,
holding said first and second component sterile in separate chambers,
mixing said components,
ensuring the thorough mixing of the components, and
introducing said mixed components into the implanted device.

In the above method, the following steps are preferably included;
stabilizing said implanted device by introducing said mixed components,
bringing said mixture to change from fluid into solid form, and
permanently defining the volume and/or shape of the device.

The method may additionally comprise the steps of;
stabilizing said device by introducing said mixed components,
repairing said leakage spontaneously after introducing said mixed component, and
allowing further adjustment of the device.

According to a preferred embodiment, freely combinable with any of the above described embodiments, said fluid is introduced into the device through an injection port.

In said method according to any one of the embodiments above, the implanted hydraulic device is preferably a powered implanted hydraulic device, and most preferably a device comprising a motor or a pump, or both.

The invention also makes available compositions for stabilizing an implanted device, wherein said composition is a sterile composition comprising a monomer or polymer, a solvent and optionally, a propellant.

Preferably said polymer is capable of forming a stable foam. Alternatively, said polymer is a thixotropic gel. Preferably, said polymer is a biocompatible polymer, and more preferably a polymer chosen among polyhydroxy acid polymers and copolymers such as poly-L-lactide, poly-DL-lactide, polyglycolide, and polydioxanone.

Preferably said polymer further comprises reinforcing particles. Said reinforcing particles are preferably chosen among biocompatible ceramic particles and fibres made up of calcium phosphates.

Further, said composition preferably comprises a cross-linker or crosslinking agent, and/or a polymerization initiator. Said composition may further comprises a propellant.

The invention also makes available a composition comprising two miscible components, wherein a first component is present in a hydraulic fluid suitable for use in an implanted hydraulic device, and a second component which is added to said fluid, wherein the two components when brought in contact with each other form a stable composition.

In this composition, said first and second component are preferably sterile and biocompatible. In one embodiment, said first component comprises a polyurethane or similar material, and said second component is a gas. Said gas is chosen from noble gases, fluorocarbons, air, nitrogen, and oxygen.

The compositions according to any one of the embodiments above, are preferably adapted for use with an implanted hydraulic device which is a powered implanted hydraulic device, and most preferably a device comprising a motor or a pump, or both.

The invention also makes available a kit for stabilizing an implanted device comprising the composition as described above, and means for introducing this into an implanted device.

In an embodiment where a first component of the composition is kept separate from a second component of the composition, said kit preferably includes a mixing chamber or device, ensuring thorough mixing of the components before they are introduced into the implanted device. Preferably the components are stored and mixed under sterile conditions.

The kit preferably comprises a temperature control device for adjusting the temperature of a component, or for maintaining temperature of at least one of the components at a predetermined value. Further, the kit preferably comprises a sterile syringe, and the sterile syringe preferably comprises a needle adapted to be introduced into an injection port.

The kit or kits according to any one of the embodiments above, are preferably adapted for use with an implanted hydraulic device which is a powered implanted hydraulic device, and most preferably a device comprising a motor or a pump, or both.

SHORT DESCRIPTION OF THE DRAWINGS

The invention will be disclosed in further detail below, in the detailed description, non-limiting examples, claims, and with reference to the attached drawings in which:

DETAILED DESCRIPTION

Figure 1:
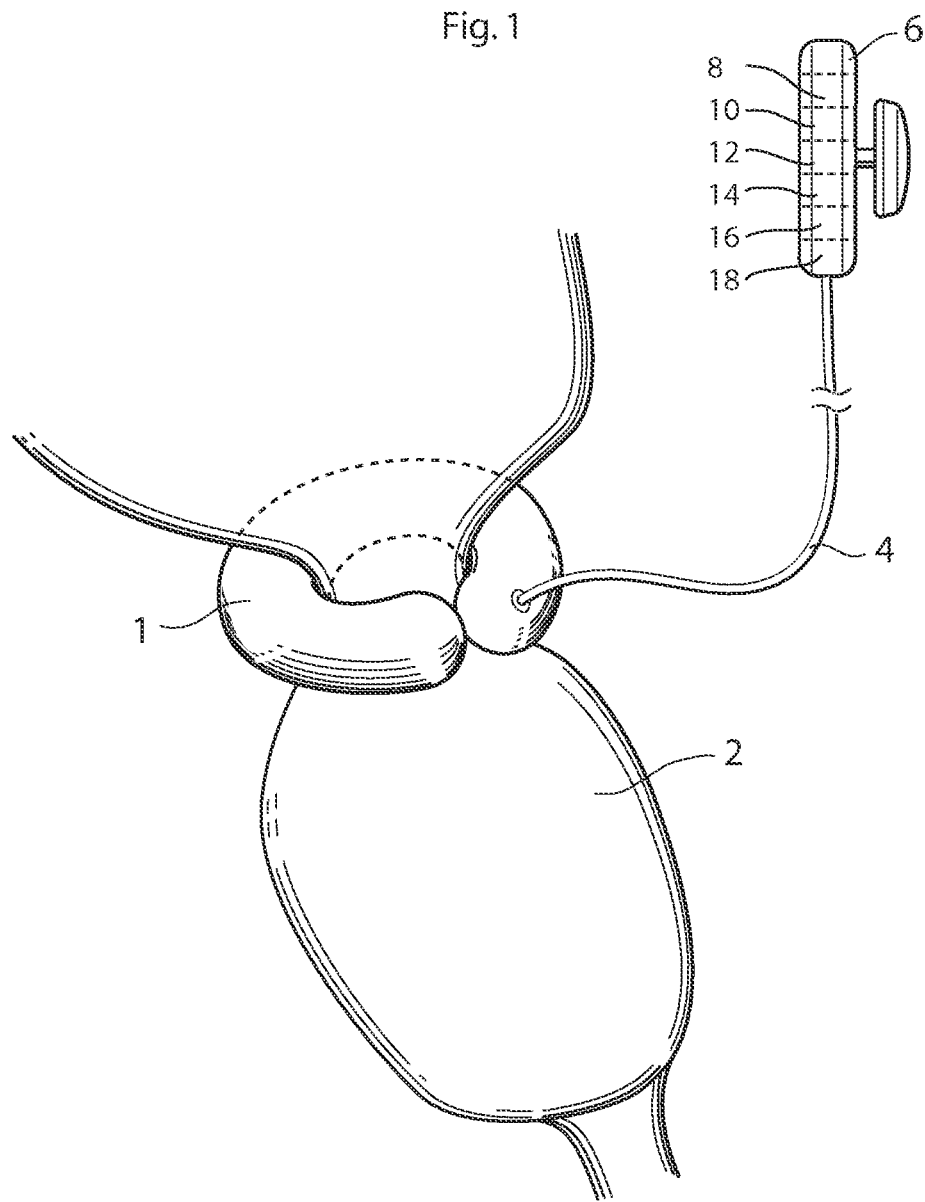
FIG. 1 shows schematically an implanted device, here an implanted hydraulic device comprising an inflatable and/or expandable substantially donut-shaped hydraulic element, arranged around a hollow organ in the body, such as but not limited to the stomach, part of the intestine or another cavity or duct in the body.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

The term "animal" encompasses all mammals and in particular humans. Similarly, the terms "treatment", "therapy", and "therapeutic use" encompass both human and animal or veterinary applications.

The term "implanted" indicates that a device or an element of a device is introduced permanently or temporarily into a human or animal body. An implanted device can be contained within the human or animal body in its entirety, or only partially, for example by being accessible through a port or other interface in the skin of said human or animal. An implanted device can be enclosed in a human or animal body in its entirety, and communicate wirelessly with an external apparatus for transmitting and receiving signals, for example transmitting measurement data and receiving control signals, and for transmitting and receiving energy. An implanted device can be a hydraulic device, an electronic device, a mechanical device, or a combination of two or more of the previous.

The term "hydraulic device" comprises any device wherein the energy that brings about the force exerted by the device, is transmitted by a hydraulic fluid acting on elements in the device. Examples of such elements include, but are not limited to hydraulic cylinders, pistons, valves, hydraulically inflatable tubes, balloons, bellows and the like. The force exerted by the device can be one of compression or restriction, achieved by a hydraulic member acting on at least one body part, organ or tissue. The hydraulic force or mechanism of action can also be one of actuation, where a hydraulic member causes a body part to move. Further examples include the filling, extending, applying torque, expanding or otherwise adjusting body parts, organs or tissue, where the hydraulic member acts on the size, shape or position of a body part, organ or tissue.

The term "biocompatible" is defined as the ability of a biomaterial to perform its desired function with respect to a medical therapy, without eliciting any undesirable local or systemic effects in the recipient or beneficiary of that therapy, but generating the most appropriate beneficial cellular or tissue response in that specific situation, and optimising the clinically relevant performance of that therapy (David F. Williams "On the mechanisms of biocompatibility" Biomaterials, Volume 29, Issue 20, July 2008, Pages 2941-2953).

The term "solidifying" refers to the transition from a liquid or flowing form, to a substantially solid, including gel-like, form. A substantially solid form also includes porous materials, such as foams and foam-like materials.

The term "initiator" is intended to encompass an initiator in the traditional sense of the word, such as a cross-linking agent, a catalyst or a polymerization agent added in a limited quantity to a fluid e.g. comprising pre-polymers, monomers etc. However, the term "initiator" is also intended to encompass examples where the initiator is an outside influence, such as radiation including for example X-rays, UV, IR, radiofrequency, ultrasound, or a change in a parameter, such as a temperature change, and the also the case where a material or material mixture capable of solidifying, is introduced and substantially replacing the fluid originally present in the implanted device.

An implanted device is schematically shown in FIG. 1, exemplified by an implanted hydraulic device comprising an inflatable and/or expandable substantially donut-shaped hydraulic element 1, arranged around a hollow organ 2 in the body, such as but not limited to the stomach, part of the intestine or another cavity or duct in the body. The device includes at least a tube 4 for introducing or withdrawing fluid to/from the hydraulic element, and a port 6 such as an injection port, to be arranged in a suitable position near the skin of the patient. The port 6 may take the form of an implantable control assembly 6, which may comprise a sensor input, a pump 8, connected to at least one fluid reservoir 10, 12, and a energy transforming member 14 connected to a receiver of wireless energy 16, placed under the skin, or an implantable energy source 18, such as a rechargeable battery.

Figure 2:
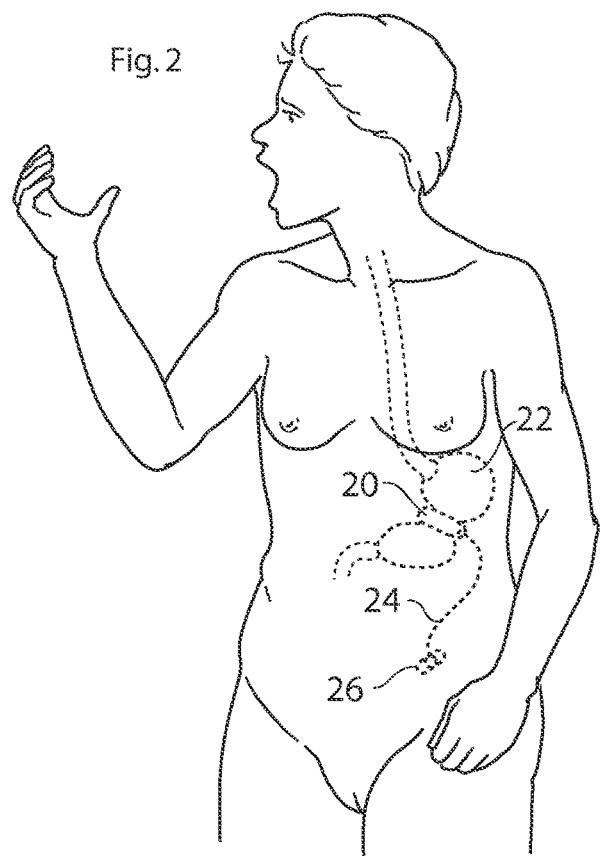
FIG. 2 shows schematically how an implanted hydraulic device is arranged on the stomach, inside the body of a human patient, said device having a tube and a port accessible through the skin of the patient.

FIG. 2 further shows schematically how a device 20 is arranged on the stomach 22, inside a human patient, said device having a tube 24 and a port 26 accessible through the skin of the patient.

One embodiment of the invention is a method for stabilizing an implanted device having an inner space enclosing a first fluid, wherein a second fluid comprising a curable component is introduced into said volume and cured in said volume. Said implanted device is selected from a hydraulic device, an electronic device, a mechanical device, or a combination of two or more of the previous. In a hydraulic device, the inner space enclosing a first fluid is mainly the hydraulic element itself, plus tubes and containers in fluid communication therewith. The fluid is preferably sterile saline, sterile air, a sterile gas or another sterile fluid. In an electronic implanted device, a mechanical implanted device or in a device combining electronic and mechanical functions, an inner space is formed around the components of the device enclosed in the outer shell of the device, preferably around moving components.

According to one embodiment of the invention, the term stabilizing involves the repair of a leak, puncture or rupture of the device, and the curable component, when cured, prevents further leakage of the fluid with retained function of the device. Curable in this context means that the fluid can transit from one state, which allows it to be introduced into the device, into another state, fulfilling its function inside the device. According to one example, the curable component is a component having thixotropic properties. The thixotropic properties result in the gel being more liquid when subjected to stress, for example when stirred or when pressed through a syringe, e.g. injected through a septum or injection port into the implanted device.

According to another embodiment of the invention, the term stabilizing involves the repair of a leak or rupture of the device and the curable component, when cured, prevents further leakage of the fluid and also permanently defines the volume and/or shape of the device. This is particularly advantageous when an implanted device no longer needs to be adjusted, but can be given its final volume and/or shape. This is also advantageous when an implanted device is under stress in the body, e.g. subjected to the weight of the patient, and needs to retain its volume and/or shape without additional energy being supplied to the device.

According to another embodiment, said first fluid is the same as said second fluid comprising a curable component, and the stabilization is initiated by adding a polymerization initiator, a catalyst, by subjecting the fluid to radiation, or by subjecting said fluid to a change in temperature. In this embodiment, the implanted device is filled with a fluid comprising a curable component, which can be stabilized at a desired point in time. Various polymerization initiators and catalysts are well known to a person skilled in the art, and a suitable initiator or catalyst can be chosen when the monomer or monomers have been chosen. The radiation can be any one of ultraviolet, infrared, and x-ray, depending on the construction and location of the implant. It is also conceived that the radiation takes place before the curable component is introduced into the device, initializing a polymerization which then continues and becomes complete inside the device.

Said second fluid is for example a fluid having a melting point sufficiently above normal body temperature to become solid at body temperature, but not as high as to compromise the health of the patient when in molten form. A suitable temperature difference is contemplated to be at least about 4° C., preferably about 6° C. or higher, depending on the location of the implanted device, surrounding tissue, and the construction of the implanted device.

According to an embodiment above, wherein the second fluid solidifies when exposed to an initiator, and wherein said hydraulic device implanted in the body does not contain said initiator, the method preferably includes the steps of:
  introducing an initiator into said fluid,
  mixing said initiator and said fluid, and
  introducing the resulting mixture into said hydraulic device.

In the above embodiment said initiator is chosen from air, nitrogen, and oxygen. Alternatively, said initiator is chosen from a polymerization initiator, a cross-linking agent, and a catalyst Further, where the initiator is a component capable of solidifying when exposed to water or moisture, water or moisture is preferably added to said component either before or after introduction of said component into the implanted device.

The initiator is preferably a biocompatible component.

In any one of the above embodiments, the initiator and at least one chamber holding the same are kept under sterile conditions. The method preferably comprises the use of a sterile reservoir containing the initiator, and further includes a step of moving the sterile initiator from said reservoir into the implanted hydraulic device under sterile conditions.

In any one of the above embodiments, the initiator and at least one chamber holding the same are kept under sterile conditions. The method preferably comprises the use of a sterile reservoir containing the initiator, and further includes a step of moving the sterile initiator from said reservoir into the implanted hydraulic device under sterile conditions.

In a method where the initiator comprises two sterile substances, the method preferably includes a step of mixing said substances under sterile conditions before the introduction of said substances into the body.

A method according to the invention preferably comprises the steps of:
keeping a first component of the initiator separated from a second component of the initiator, both components being biocompatible materials,
holding said first and second component sterile in separate chambers,
mixing said components,
ensuring the thorough mixing of the components, and
introducing said mixed components into the implanted device.

In the above method, the following steps are preferably included;
stabilizing said implanted device by introducing said mixed components,
bringing said mixture to change from fluid into solid form, and
permanently defining the volume and/or shape of the device.

The method may additionally comprise the steps of;
stabilizing said device by introducing said mixed components,
repairing said leakage spontaneously after introducing said mixed component, and
allowing further adjustment of the device.

According to a preferred embodiment, freely combinable with any of the above described embodiments, said fluid is introduced into the device through an injection port.

Figure 3:
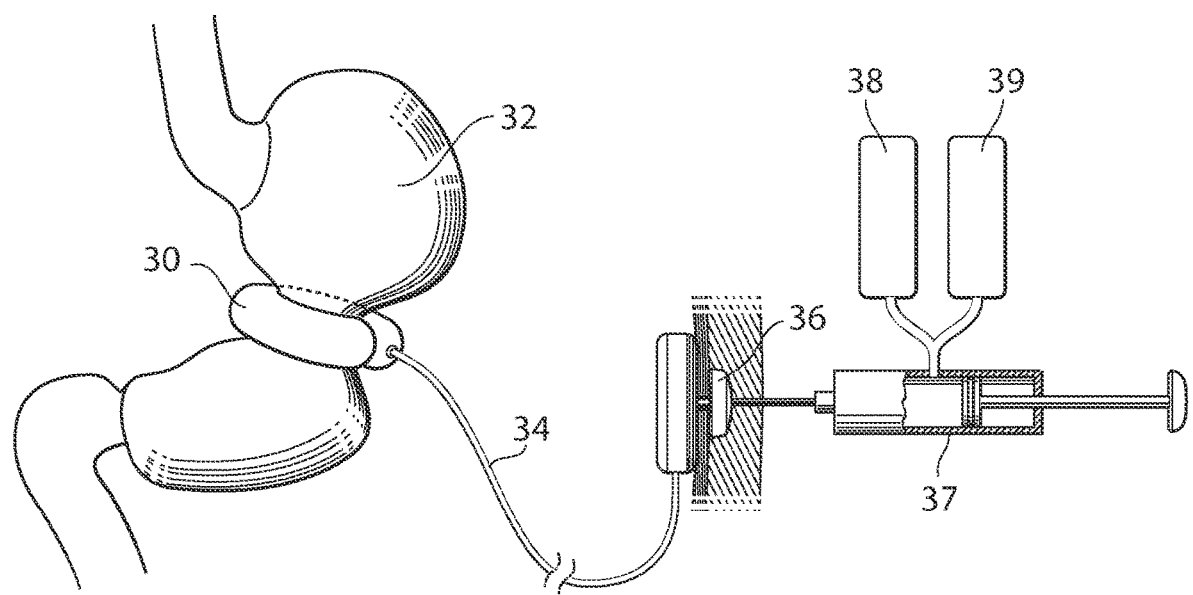
FIG. 3 shows schematically a detail view, where an implanted hydraulic device is arranged on an organ, said device having a tube and an injection port placed at an accessible site on the body, e.g. the skin of a patient. An injection device is shown, connected to two containers containing for example a sealing component and a propellant, or a sealing component and a polymerization initiator.

This is illustrated in FIG. 3, which shows schematically a detail view, where an implanted hydraulic device 30 is arranged on an organ 32, said device having a tube 34 and an injection port 36 placed at an accessible site on the body, e.g. the skin of a patient. An injection device 37 is shown, connected to two containers 38 and 39 containing for example a sealing component and a propellant, or a sealing component and a polymerization initiator. Said sealing component and propellant, or sealing component and initiator are mixed in the injection device 37 before being introduced through the port 36 and tube 34 into the device 30. The sealing component cures in situ in the device 30 repairing possible leaks, and the propellant aids in the mixing, transport and curing of the sealing components, and helps to restore and maintain a desired pressure in the device.

Figure 4:
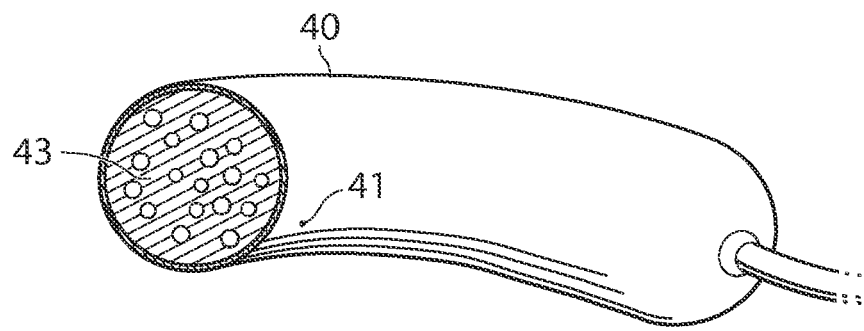
FIG. 4 shows schematically an embodiment where an implanted hydraulic device having a small leak has been filled with a foam which closes the leak and fills the device.

An embodiment of the invention is schematically shown in FIG. 4, where an implanted hydraulic device 40 having a small leak 41 has been filled with a foam 43 which closes the leak, fills the device, and also maintains the desired properties of the device, such as a desired shape, volume, rigidity, pressure, orientation etc.

Figure 5:
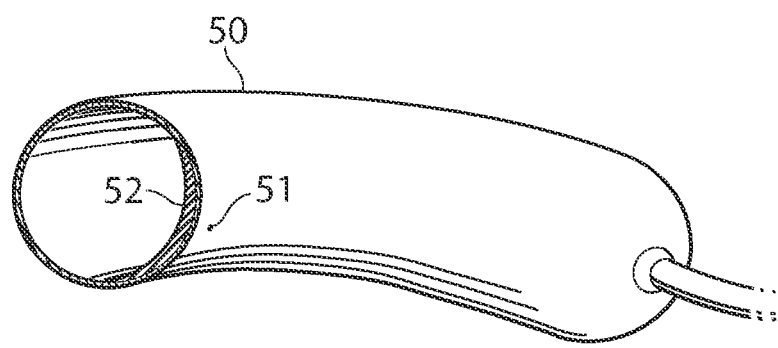
FIG. 5 shows schematically another embodiment where an implanted hydraulic device having a small leak has been repaired by the introduction of a sealing component which forms a layer on the inside of the device, closing the leak.

Another embodiment is schematically shown in FIG. 5, where an implanted hydraulic device 50 having a small leak 51 has been repaired by the introduction of a sealing component which forms a layer 52 on the inside of the device, closing the leak. The properties of the device, such as a desired shape, volume, rigidity, pressure, orientation etc can still be adjusted by introducing or withdrawing fluid to/from the device.

In said method according to any one of the embodiments above, the implanted hydraulic device is preferably a powered implanted hydraulic device, and most preferably a device comprising a motor or a pump, or both. A motor in this context can be a stepping motor, a high-frequency/low-torque motor, a low-frequency/high-torque motor, a brushless motor etc.

Similarly, a pump is chosen among positive displacement pumps, such as but not limited to diaphragm pumps, piston pumps, screw feeders, plunger pumps, gear pumps; and centrifugal pumps, such as but not limited to impeller pumps.

The invention also makes available compositions for stabilizing an implanted device, wherein said composition is a sterile composition comprising a monomer or polymer, a solvent and optionally, a propellant.

Preferably said polymer is capable of forming a stable foam, foam-like material, a solid or porous material. Alternatively, said polymer is a thixotropic gel. Preferably, said polymer is a biocompatible polymer, and more preferably a polymer chosen among polyhydroxy acid polymers and copolymers such as poly-L-lactide, poly-DL-lactide, polyglycolide, and polydioxanone.

Preferably said polymer further comprises reinforcing particles. Said reinforcing particles are preferably chosen among biocompatible ceramic particles and fibres made up of calcium phosphates.

Further, said composition preferably comprises a crosslinker or crosslinking agent, and/or a polymerization initiator. Said composition may further comprises a propellant.

Propellants useful in the present invention comprise, but are not limited to, compressed gases, such as compressed air, nitrogen, oxygen or noble gases; liquefied propellants such as liquefied propane, isobutene, n-butane or a mixture thereof, dimethyl ether; or chlorofluorocarbons.

One embodiment of the invention is a composition which comprises two miscible components, wherein a first component is present in the hydraulic fluid, and a second component is added to said fluid, and the two components when brought in contact with each other form a stable composition. Preferably said first and second component are sterile. Preferably said first and second component are biocompatible.

In the above embodiment, said first component preferably comprises polyurethane, and said second component is preferably a gas. Said gas is chosen from air, nitrogen, and oxygen.

A composition according to any one of the embodiments above, is preferably a composition adapted for use with an implanted hydraulic device which is a powered implanted hydraulic device, and most preferably a device comprising a motor or a pump, or both. The adaptation of the composition may be an adjustment or replacement of one or more of its chemical or physical properties. A composition for use with or in a powered implanted hydraulic device should not be corrosive or flammable, and it is conceived that its rheological properties need to be adjusted.

The invention also makes available a kit for stabilizing an implanted device comprising the composition as described above, and means for introducing this into an implanted device.

In an embodiment where a first component of the composition is kept separate from a second component of the composition, said kit preferably includes a mixing chamber or device, ensuring thorough mixing of the components before they are introduced into the implanted device. Preferably the components are stored and mixed under sterile conditions.

The kit preferably comprises a temperature control device for adjusting the temperature of a component, or for maintaining temperature of at least one of the components at a predetermined value. Further, the kit preferably comprises a sterile syringe, and the sterile syringe preferably comprises a needle adapted to be introduced into an injection port.

Further still, the kit or kits according to any one of the embodiments above, are preferably adapted for use with an implanted hydraulic device which is a powered implanted hydraulic device, and most preferably a device comprising a motor or a pump, or both.

Figure 6:
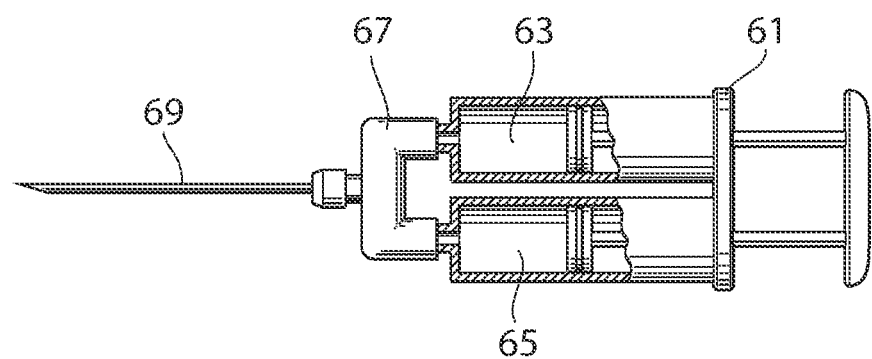
FIG. 6 shows schematically a device with two compartments for holding two components, together forming a mixture capable of sealing a leak, such as a polymer mixture and a polymerization initiator, connected to means for bringing the two components in contact with each other, preferably mixing them thoroughly, and means for introducing them into the hydraulic device.

FIG. 6 illustrates one embodiment by schematically showing a device 61 with two compartments 63 and 65 for holding two components, together forming a mixture capable of sealing a leak, such as a polymer mixture and a polymerization initiator, connected to means 67 for bringing the two components in contact with each other, preferably mixing them thoroughly, and means 69 for introducing them into the hydraulic device, e.g. a syringe for penetrating an injection port. Please observe that special needles are needed for injecting into an injection port. Such a needle has the opening on the side thus not cutting out a hole in the membrane, not included in the picture.

In a method, composition or kit according to the invention or according to one or more of the above embodiments above, a variety of polymers can be used. The choice of polymer, polymer mixture or copolymers suitable for forming a foam for use in the present invention depends on many factors, such as curing time, mechanical strength, and biocompatibility.

Examples of suitable biocompatible polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups, poly(anhydrides), polyphosphazenes, biomolecules (i.e. biopolymers such as collagen, elastin, bioabsorbable starches and the like) and blends thereof. For the purpose of this invention, aliphatic polyesters include but are not limited to homopolymers and copolymers of lactide (which includes lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonate) for the purpose of this invention include those described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in "Journal of Biomaterials Research", Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include those mentioned in U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and epsilon-caprolactone described inter alia by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons.

Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (which are incorporated herein by reference). Polyorthoesters such as those described by Heller in Handbook of Biodegradable Polymers, edited by Domb, Kost and Wisemen, Hardwood Academic Press, 1997, pages 99-118 (hereby incorporated herein by reference).

Gradient foams are currently a promising approach in may therapeutic application, for example for repairing or restoring tissue, promoting regrowth of tissue, acting as scaffolds for tissue growth etc. Aliphatic polyesters are the absorbable polymers that are currently preferred for making gradient foams. Aliphatic polyesters can be homopolymers, copolymers (random, block, segmented, tappered blocks, graft, triblock, etc.) having a linear, branched or star structure. Preferred are linear copolymers. Suitable monomers for making aliphatic homopolymers and copolymers may be selected from the group consisting of, but are not limited to, lactic acid, lactide (including L-, D-, meso and D,L mixtures), glycolic acid, glycolide, epsilon-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

Elastomeric copolymers are also particularly useful in the present invention. Suitable bioabsorbable biocompatible elastomers include but are not limited to those selected from the group consisting of elastomeric copolymers of epsilon-caprolactone and glycolide (preferably having a mole ratio of epsilon-caprolactone to glycolide of from about 35:65 to about 65:35, more preferably from 45:55 to 35:65) elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably from 45:55 to 30:70 or from about 95:5 to about 85:15) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of epsilon-caprolactone and p-dioxanone (preferably having a mole ratio of epsilon-caprolactone to p-dioxanone of from about from 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. Examples of suitable bioabsorbable elastomers are described in U.S. Pat. Nos. 4,045,418; 4,057,537 and 5,468,253 all hereby incorporated by reference. These elastomeric polymers will have an inherent viscosity of from about 1.2 dL/g to about 4 dL/g, preferably an inherent viscosity of from about 1.2 dL/g to about 2 dL/g and most preferably an inherent viscosity of from about 1.4 dL/g to about 2 dL/g as determined at 25 DEG C. in a 0.1 gram per deciliter (g/dL) solution of polymer in hexafluoroisopropanol (HFIP).

Different solvents can be used in the present invention. The choice of solvent is dependent on the choice of polymer, and within the capabilities of a skilled person without an inventive effort. When the polymer is an absorbable aliphatic polyester, suitable solvents include solvents selected from a group consisting of formic acid, ethyl formate, acetic acid, hexafluoroisopropanol (HFIP), cyclic ethers (i.e. THF, DMF, and PDO), acetone, acetates of $C_2$ to $C_5$ alcohol (such as ethyl acetate and t-butylacetate), glyme (i.e. monoglyme, ethyl glyme, diglyme, ethyl diglyme, triglyme, butyl diglyme and tetraglyme) methylethyl ketone, dipropyleneglycol methyl ether, lactones (such as gamma-valerolactone, delta-valerolactone, beta-butyrolactone, gamma-butyrolactone) 1,4-dioxane, 1,3-dioxolane, 1,3-dioxolane-2-one (ethylene carbonate), dimethylcarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4-dioxane. A homogeneous solution of the polymer in the solvent is prepared using standard techniques.

It is preferred that the components are biocompatible. In some embodiments, it may further be desirable that the polymer—if it escapes from the hydraulic device—can be safely resorbed in the animal body. A skilled person is aware of available resorbable polymers, and is capable of choosing an appropriate polymer, or a mixture of two or more polymers, after receiving the guidance given in the present description and common general knowledge in the relevant field.

According to an embodiment of the invention, the method comprises mixing a first solution of fibrinogen and a second solution of thrombin immediately before introducing into the hydraulic device. In this embodiment, saline is the preferred solvent.

The invention offers many advantages, as the patient does not have to be hospitalized or subjected to surgical intervention. The method according to the invention can be practiced in an out-patient setting, at a general practitioners office, by a nurse, paramedic or possibly even by the patient himself/herself.

The invention offers a not only a reduction of the time and cost for repairing an implanted hydraulic device, but also significant benefits for the patient in terms of reduced strain, suffering and risk of post-operative complications.

One embodiment of the invention offers the additional advantage of making it possible to stabilize the shape, volume or position of a hydraulic element in the body, making it possible to leave the element in place without it loosing its function with respect to the shape, volume or position. A further embodiment is that the hydraulic element itself is stabilized and left in place, whereas the remaining components of the implanted device, such as tubes, control means, ports etc. are surgically removed.

EXAMPLES

In Vitro Experiments

1. Repairing a Leak in an Air-Filled Hydraulic Device Using a Foam-Forming Polymer A commercially available laparoscopic gastric band is purchased and applied to a glass cylinder and inflated with air to a degree that it firmly grips the cylinder. The band and cylinder are immersed in physiological saline in a large laboratory beaker. The tube and injection port are left hanging outside the beaker. A leak is simulated by pricking the inflated band with a fine needle. The slow formation of bubbles will indicate that the inflated band is leaking. After a while, the device no longer grips the cylinder as firmly as before. A mixture of polyurethane, butane and air is injected into the device through the injection port. After 10 minutes, the formation of bubbles ceases, the device becomes rigid, and grips the cylinder as firmly as before.

2. Repairing a Leak in an Air-Filled Hydraulic Device Using a Thixotropic Gel

The set-up above is repeated with the difference that a thixotropic gel is used. In the experimental set-up the device is agitated or massaged gently to spread the gel inside the device. The absence of bubbles indicates that the leak has been repaired. The volume and shape of the device can still be regulated by varying the pressure by introducing or removing air from the device.

In a clinical setting, a device implanted in soft tissue, near the skin, may be manipulated through the skin. An implant, located deeper in the body is not accessible from the outside, but the spreading of the thixotropic gel can be facilitated if the patient changes position, e.g. lies down and turns from a supine to a prostrate position. Alternatively, in the case of an implanted device which is controlled wirelessly, or transdermally, it is conceived that the device is operated, e.g. expanded and contracted slightly, in order to facilitate the even spreading of the gel on its inside surfaces.

3. Repairing a Leak in a Hydraulic Device Filled with Saline, Using a Foam-Forming Polymer The set-up above is repeated with the difference that the device is filled with saline to which Coomassie blue has been added, and that the saline is withdrawn partially or totally before introduction in order to prevent excessive pressure build-up in the device. The presence of blue colour in the surrounding water indicates a leak, and the absence of colour indicates successful repair. As the cured foam replaces the saline inside the device, the volume and shape of the device becomes rigid and further adjustments are no longer possible.

4. Repairing a Leak in a Hydraulic Device Filled with Saline Using a Thixotropic Gel The set-up according to Example 3 is repeated with the difference that a thixotropic gel is used. When the band is pricked with the needle, a faint flow of bluish fluid shows the location of the leak. A thixotropic gel is introduced into the device, which is massaged gently to spread the gel inside the device. The saline in the beaker is replaced and the location of the leak is observed. The absence of coloured leakage indicates that the hole has been successfully repaired. The volume and shape of the device can still be regulated by varying the pressure, introducing or removing saline from the device.

5. Fixating the Shape of an Implanted Hydraulic Device

An experimental hydraulic brace is constructed by attaching a hydraulic device in the shape of a fluid-filled cylinder to two metal rods connected to a digital force gauge. The device is inflated until the desired force is registered. The device is punctured and then repaired using a foam-forming polymer as above, in examples 1 and 3. After curing, the force exerted by the device is determined again, and it is determined if the foam-filled device is capable of maintaining the force of the intact hydraulic device.

Similarly, punctured and repaired hydraulic devices can be tested using commercially available pull testers and compression testers, such as the Mark-10 product range, marketed by Mark-10 Corporation, Copiage, N.Y., USA.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

The invention claimed is:

1. A method for stabilizing a leaking implanted device capable of being hydraulically adjusted by introducing hydraulic fluid to and withdrawing hydraulic fluid from the device, the device having an inner space for enclosing the hydraulic fluid, the method comprising:
repairing a leakage, puncture or rupture of the implanted hydraulically adjustable device by the introduction of a sealing component which forms a layer on the inside of the implanted hydraulically adjustable device preventing further leakage with retained function of the device, such that the repaired implanted hydraulically adjustable device can be hydraulically adjusted by introducing hydraulic fluid to and withdrawing hydraulic fluid from the device.

2. The method according to claim 1, wherein the leaking implanted hydraulically adjustable device comprises an injection port, and wherein:
repairing the implanted hydraulically adjustable device by the introduction of a sealing component which forms a layer on the inside closing the leak with retained function of the device, such that the repaired implanted hydraulically adjustable device can be hydraulically adjusted by introducing or withdrawing fluid to/from the device,
comprises injecting into the injection port.

3. The method according to claim 1, further comprising the step of hydraulically adjusting the repaired implant.

4. The method according to claim 1, wherein said implanted hydraulic device is a powered implanted hydraulic device comprising at least one of a motor and a pump.

5. A method for stabilizing a leaking implanted device, the device comprising a hydraulic element and an implantable control assembly such that the hydraulic element can be non-invasively hydraulically adjusted by introducing hydraulic fluid to and withdrawing hydraulic fluid from the hydraulic element using the control assembly, the device having an inner space for enclosing the hydraulic fluid, the method comprising: introducing at least one of: a solidifying fluid, an initiator adapted to exert influence on a solidifying fluid or the hydraulic fluid, and a mixture of a solidifying fluid and an initiator, into said leaking implanted hydraulically adjustable device for solidifying the solidifying fluid or the hydraulic fluid for permanently defining the volume and/or shape of the device, thereby disabling the function of the control assembly.

6. The method according to claim 5, further comprising the step of mixing a solidifying fluid and an initiator prior to the introduction into said leaking implanted hydraulically adjustable device.

7. The method according to claim 5, wherein the leaking implanted hydraulically adjustable device comprises an injection port, and wherein: introducing at least one of: a solidifying fluid, an initiator adapted to exert influence on a solidifying fluid, and a mixture of a solidifying fluid and an initiator, into said leaking implanted hydraulically adjustable device for permanently defining the volume and/or shape of the device, comprises injecting into the injection port.

8. The method according to claim 5, wherein said solidifying fluid comprises a curable component, and the initiator added to said fluid is chosen from a polymerization initiator, a cross-linking agent, and a catalyst.

9. The method according to claim 5, wherein said implanted hydraulic device is a powered implanted hydraulic device comprising at least one of a motor and a pump.

10. The method according to claim 5, further comprising the step of hydraulically adjusting the repaired implant.

11. The method according to claim 5, wherein said solidifying fluid comprises a curable component adapted to solidify when exposed to radiation, and wherein the method further comprises exposing the solidifying fluid to radiation for initiating solidification.

* * * * *